(12) United States Patent
Legrand et al.

(10) Patent No.: US 7,217,298 B2
(45) Date of Patent: May 15, 2007

(54) READY-TO-USE BLEACHING COMPOSITIONS, PREPARATION PROCESS AND BLEACHING PROCESS

(75) Inventors: Fréderic Legrand, Courbevoie (FR); Sylvain Kravtchenko, Asnieres (FR)

(73) Assignee: L'Oreal S.A., Paris (FR)

(*) Notice: Subject to any disclaimer, the term of this patent is extended or adjusted under 35 U.S.C. 154(b) by 234 days.

(21) Appl. No.: 10/758,265

(22) Filed: Jan. 16, 2004

(65) Prior Publication Data
US 2004/0235700 A1    Nov. 25, 2004

Related U.S. Application Data

(60) Provisional application No. 60/441,320, filed on Jan. 22, 2003.

(30) Foreign Application Priority Data
Jan. 16, 2003    (FR)    ................................. 03 00456

(51) Int. Cl.
D06L 3/00    (2006.01)
(52) U.S. Cl. ...................... 8/405; 8/101; 8/107; 8/109; 8/111; 8/431; 8/552; 8/554; 8/561; 8/617; 424/62; 132/202; 132/208
(58) Field of Classification Search ................... 8/111, 8/431, 531, 552, 554, 561, 617, 101, 107, 8/109; 132/208, 202; 424/62
See application file for complete search history.

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/28 |
| 2,273,780 A | 2/1942 | Dittmar | 260/28 |
| 2,375,853 A | 5/1945 | Kirby et al. | 260/383 |
| 2,388,614 A | 11/1945 | Kirby et al. | 167/22 |
| 2,454,547 A | 11/1948 | Bock et al. | 255/587.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,472,840 A | 10/1969 | Stone et al. | 260/231 |
| 3,836,537 A | 9/1974 | Boerwindle et al. | 260/29.6 |
| 3,874,870 A | 4/1975 | Green et al. | 71/67 |
| 3,915,921 A | 10/1975 | Schlatzer, Jr. | 260/17.4 |
| 3,929,990 A | 12/1975 | Green et al. | 424/78 |
| 3,966,904 A | 6/1976 | Green et al. | 424/78 |
| 4,001,432 A | 1/1977 | Green et al. | 424/78 |
| 4,005,193 A | 1/1977 | Green et al. | 424/168 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567 |
| 4,027,020 A | 5/1977 | Green et al. | 424/248.56 |
| 4,031,307 A | 6/1977 | DeMartino et al. | 536/114 |
| 4,131,576 A | 12/1978 | Iovine et al. | 260/17.4 |
| 4,157,388 A | 6/1979 | Christiansen | 424/70 |
| 4,509,949 A | 4/1985 | Huang et al. | 586/558 |
| 4,540,510 A | 9/1985 | Karl | 252/35.8 |
| 4,702,906 A | 10/1987 | Jacquet et al. | 424/70 |
| 4,719,282 A | 1/1988 | Nadolsky et al. | 528/310 |
| 4,839,166 A | 6/1989 | Grollier et al. | 424/71 |
| 4,927,627 A | 5/1990 | Schrader et al. | 424/62 |
| 5,089,578 A | 2/1992 | Valint et al. | 526/240 |
| 5,888,484 A | 3/1999 | Schmitt et al. | 424/62 |
| 6,379,401 B1 * | 4/2002 | Legrand et al. | 8/431 |
| 2003/0036490 A1 * | 2/2003 | Lorant et al. | 510/130 |
| 2004/0074015 A1 | 4/2004 | Kravtchenko et al. | 8/406 |

FOREIGN PATENT DOCUMENTS

| | | |
|---|---|---|
| DE | 197 23 538 | 9/1998 |
| EP | 0 122 324 | 10/1984 |
| EP | 0 216 479 | 4/1987 |
| EP | 0 337 354 | 10/1989 |
| EP | 0 750 899 | 1/1997 |
| FR | 1 400 366 | 5/1965 |
| FR | 1 492 597 | 8/1967 |
| FR | 1 583 363 | 10/1969 |

(Continued)

OTHER PUBLICATIONS

English language Derwent Abstract of DE 197 23 538.

(Continued)

*Primary Examiner*—Eisa Elhilo
(74) *Attorney, Agent, or Firm*—Finnegan Henderson Farabow Garrett & Dunner LLP

(57) ABSTRACT

A composition comprising:
i) at least one anhydrous bleaching composition in paste form comprising
   at least one peroxygenated salt,
   at least one alkaline agent, and
   from 15% to 35% by weight of at least one inert organic liquid, and
ii) at least one oxidizing composition in the form of a hydrogen peroxide oil-in-water emulsion comprising
   at least one surfactant chosen from nonionic and anionic surfactants and
   at least one copolymer comprising at least one hydrophobic unit and at least one unit derived from at least one ethylenically unsaturated monomer comprising at least one sulphonic group, in free or partially or totally neutralized form.

The composition may, for example, be used for bleaching human keratin fibers, such as hair.

Also disclosed is a process for preparing a ready-to-use composition, comprising mixing, before use, the bleaching composition with the oxidizing composition.

64 Claims, No Drawings

FOREIGN PATENT DOCUMENTS

| | | |
|---|---|---|
| FR | 2 080 759 | 11/1971 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 413 907 | 8/1979 |
| FR | 2 470 596 | 6/1981 |
| FR | 2 519 863 | 7/1983 |
| FR | 2 598 611 | 11/1987 |
| FR | 2 633 940 | 1/1990 |
| FR | 2 162 025 | 7/1993 |
| FR | 2 788 974 | 8/2000 |
| FR | 2 788 976 | 8/2000 |
| FR | 2 818 543 | 6/2002 |
| GB | 1 021 400 | 3/1966 |
| JP | A 1-106813 | 4/1989 |
| JP | A 9-20615 | 1/1997 |
| JP | A 11-012140 | 1/1999 |
| JP | A 9-157142 | 6/1999 |
| JP | A 2000-309518 | 11/2000 |
| WO | WO 00/31154 | 6/2000 |
| WO | WO 02/51369 | 7/2002 |

OTHER PUBLICATIONS

English language Derwent Abstract of FR 2 633 940.
English language Derwent Abstract of FR 2 270 846.
English language Derwent Abstract of FR 2 383 660.
English language Derwent Abstract of FR 2 598 611.
English language Derwent Abstract of FR 2 470 596.
English language Derwent Abstract of FR 2 519 863.
English language Derwent Abstract of FR 2 788 974.
English language Derwent Abstract of FR 2 788 976.
English language Derwent Abstract of FR 2 162 025.
English language Derwent Abstract of FR 2 280 361.
English language Derwent Abstract of FR 2 252 840.
English language Derwent Abstract of FR 2 368 508.
English language Derwent Abstract of FR 2 080 759.
English language Derwent Abstract of FR 2 190 406.
English language Derwent Abstract of FR 2 320 330.
English language Derwent Abstract of FR 2 316 271.
English language Derwent Abstract of FR 2 336 434.
English language Derwent Abstract of FR 2 413 907.
English language Derwent Abstract of FR 2 818 543.
English language Derwent Abstract of FR 1 583 363.
English language Derwent Abstract of JP 1-106813.
English language Derwent Abstract of JP A 9-157142.
English language Derwent Abstract of JP A 11-12140.
Notice of Rejection dated May 24, 2005, Japanese Patent Application No. 2004-009901.
Y. Morishima, "Self-Assembling Amphiphilic Polyelectrolytes And Their Nanostructures", Dept. of Macromolecular Science, Graduate School of Science, Osaka University, Toyonaka, Osaka, Chinese Journal of Polymer Science, vol. 18, No. 40, 2000, pp. 323-336.
T. Noda et al., "Micelle Formation of Random Copolymers of Sodium 2-(Acrylamido)-2-methylpropanesulfonate and a Nonionic Surfactant Macromonomer in Water as Studied by Fluorescence and Dynamic Light Scattering", Dept. of Macromolecular Science, Graduate School of Science, Osaka University, Toyonaka, Osaka, Macromolecules 2000, 33, pp. 3694-3704.
T. Noda et al., "Solution Properties of Micelle Networks Formed by Nonionic Surfactant Moieties Covalently Bound to a Polyelectrolyte: Salt Effects on Rheological Behavior", Dept. of Macromolecular Science, Graduate School of Science, Osaka University, Toyonaka, Osaka, Langmuir, 2000, 16, pp. 5324-5332.
T. Noda et al., "Stimuli-Responsive Amphiphilic Copolymers of Sodium 2-(Acrylamido)-2-Methylpropanesulfonate and Associative Macromonomers", Dept. of Macromolecular Science, Graduate School of Science, Osaka University, Toyonaka, Osaka, pp. 220-221.
G. Fonnum et al., "Associative Thickeners. Part I: Synthesis, Rheology and Aggregation Behavior", Colloid & Polymer Science, Apr. 1993, pp. 380-389, vol. 271, No. 4.
A. Kobayashi et al., "Solubilization Properties of N-substituted Amphiphilic Acrylamide Copolymers", Journal of Applied Polymer Science, vol. 73, No. 12, Sep. 19, 1999, pp. 2447-2453.

* cited by examiner

READY-TO-USE BLEACHING COMPOSITIONS, PREPARATION PROCESS AND BLEACHING PROCESS

This application claims benefit of U.S. Provisional Application No. 60/441,320, filed Jan. 22, 2003 and French Application No. 0300456, filed Jan. 16, 2003.

Disclosed herein is a composition for bleaching keratin fibers, a process for bleaching keratin fibers using the composition and a multi-compartment device comprising the composition.

It is a known practice to bleach human keratin fibers, such as hair, using bleaching compositions comprising at least one oxidizing agent. Examples of oxidizing agents conventionally used, include hydrogen peroxide or compounds capable of producing hydrogen peroxide by hydrolysis, for instance, urea or persalts, such as perborates, persulphates and percarbonates.

Originally, bleaching compositions were in powder form, i.e., pulverulent compositions. However, they had the drawback of producing dust during their handling, transportation and storage. Furthermore, this phenomenon could be aggravated by the fact that the products of which these powders were composed could be corrosive and irritant to the eyes, the respiratory pathways and mucous membranes. Accordingly, in order to solve at least some of these problems encountered during the use of pulverulent compositions, bleaching compositions in paste form have recently been developed. Thus, the pulverulent compounds are dispersed in a thickened organic inert liquid support.

Although this presentation form can provide a solution to the volatility problems mentioned above, the use of compositions in paste form may result in new difficulties.

Thus, the bleaching compositions, whether in powder or paste form, may need to be mixed before use with aqueous hydrogen peroxide compositions in order to obtain the ready-to-use bleaching composition.

These aqueous hydrogen peroxide compositions may be in the form of aqueous solutions or oil-in-water emulsions and may be more or less liquid or fluid.

This presentation form may favor mixtures with bleaching compositions in powder form, because the more liquid or fluid the aqueous hydrogen peroxide composition, the more quickly and easily the bleaching powder dissolves.

On the other hand, bleaching compositions in paste form lack water and their texture may be compact and hard. Furthermore, usually these bleaching pastes are of hydrophobic nature given the presence of a high content of inert organic liquid. Consequently, the mixing of the bleaching composition and of the hydrogen peroxide composition may not be easy. This may be reflected not only by a longer mixing time but also by a complication of the operations to obtain a uniform mixture.

One of the solutions envisaged was to enrich the hydrogen peroxide oil-in-water emulsions with fatty substances such as fatty alcohols, in order to obtain more compact cream textures. However, there is a great difference in texture between many of these compositions and anhydrous bleaching pastes, and the mixtures may take a relatively long time to prepare.

Thus it may be beneficial, in some application, to find oxidizing aqueous compositions which mix with bleaching pastes more quickly and more easily.

Thus, disclosed herein is a composition for bleaching human keratin fibers, such as the hair, which can be obtained by mixing before use comprising:
i) at least one anhydrous bleaching composition comprising
    at least one peroxygenated salt,
    at least one alkaline agent, and
    from 15% to 35% by weight of at least one inert organic liquid, and
ii) at least one oxidizing composition comprising
    at least one surfactant chosen from nonionic and anionic surfactants and
    at least one copolymer comprising at least hydrophobic unit and at least one unit derived from at least one ethylenically unsaturated monomer comprising at least one sulphonic group, in free or partially or totally neutralized form.

In one embodiment, the at least one anhydrous bleaching composition is in paste form.

In one embodiment, the at least one oxidizing composition is in the form of a hydrogen peroxide oil-in-water emulsion.

In one embodiment, the ready-to-use composition comprises at least one anhydrous bleaching composition and the at least one oxidizing composition.

Further disclosed herein is a process for preparing the composition, comprising mixing before use the at least one anhydrous bleaching composition, in paste form, and with the at least one oxidizing composition.

Even further disclosed herein is a process for bleaching human keratin fibers, such as hair, comprising applying the at least one ready-to-use bleaching composition, as disclosed herein, to the area of wet or dry human keratin fibers to be bleached; leaving the at least one ready-to-use composition to act for a leave-in time that is sufficient to obtain the desired bleaching; removing the at least one ready-to-use composition from the human keratin fibers by rinsing with water, washing the human keratin fibers with shampoo, and optionally drying the human keratin fibers.

Also disclosed herein is a multi-compartment device, or "kit", for performing the abovementioned bleaching process, comprising at least two compartments, wherein
    at least one compartment comprises at least one anhydrous bleaching composition comprising
    at least one peroxygenated salt,
    at least one alkaline agent, and
    from 15% to 35% by weight of at least one inert organic liquid, and at least one oxidizing composition comprising
    at least one surfactant chosen from nonionic and anionic surfactants and
    at least one copolymer comprising at least one hydrophobic unit and at least one unit derived from at least one ethylenically unsaturated monomer comprising at least one sulphonic group, in free or partially or totally neutralized form and comprising at least one hydrophobic unit.

In one embodiment, the at least one anhydrous bleaching composition is in paste form.

In one embodiment, the at least one oxidizing composition is in the form of a hydrogen peroxide oil-in-water emulsion.

It has been found that some embodiments of mixtures of the at least one anhydrous bleaching composition in paste form with at least one hydrogen peroxide oil-in-water emulsions comprising at least surfactant chosen from nonionic and anionic surfactants and at least one copolymer as described above, may be prepared significantly more quickly and more easily.

Furthermore, some of the compositions disclosed herein may be easy and quick to apply. These compositions may, for example, show very good adhesion and may not run outside the areas that it is desired to bleach.

In one embodiment, the disclosed bleaching compositions may also allow strong, uniform bleaching results, while at the same time may afford at least one very good cosmetic property.

The at least one anhydrous bleaching composition will first be described.

Anhydrous Bleaching Composition

In one embodiment, the at least one anhydrous composition may be in paste form. For example, the at least one anhydrous composition may comprise less than or equal to 1% by weight of water, relative to the total weigh of the paste and, further, for example, less than or equal to 0.5% by weight of water, relative to the total weight of the paste.

Peroxygenated Salt

The at least one peroxygenated salt, may be chosen, for example, from persulfates, perborates, percarbonates and peroxides of alkali metals and alkaline-earth metals, for instance, sodium, potassium and magnesium.

In one embodiment, the at least one peroxygenated salt is a persulphate, such as sodium persulphate and potassium persulphate.

For example, the content of the at least one peroxygenated salt in the at least one anhydrous bleaching composition may be present in an amount ranging from 10% to 70% by weight, relative to the total weight of the at least one anhydrous bleaching composition, and further, for example, from 20% to 60% by weight, relative to the total weight of the at least one anhydrous bleaching composition. Also, for example, the at least one peroxygenated salt may be present in the composition disclosed herein, in an amount ranging from 5% to 35% by weight, relative to the total weight of the composition (i.e. comprising the mixture of the at least one anhydrous bleaching composition and the at least one oxidizing composition) and further, for example, from 10% to 30% by weight, relative to the total weight of the composition.

Alkaline Agents

In one embodiment, the at least one anhydrous bleaching composition also comprises at least one alkaline agent, which may, for example, be chosen from urea; ammonium salts, for instance, chlorides, sulphates, phosphates and nitrates; and alkali metal (such as, for example, sodium and potassium) and alkaline-earth metal (such as, for example, magnesium) silicates, phosphates and carbonates.

For example, the at least one alkaline agent in the at least one anhydrous bleaching composition may be present in an amount ranging from 0.01% to 40% by weight, relative to the total weight of the at least one anhydrous bleaching composition and further, for example, from 0.1% to 30% by weight, relative to the total weight of the at least one anhydrous bleaching composition. In one embodiment, the at least one alkaline agent in the composition disclosed herein, is present in an amount ranging from 0.005% to 20% by weight, relative to the total weight of the composition, and further, for example from 0.05% to 15% by weight, relative to the total weight of the composition.

Inert Liquid

The at least one anhydrous bleaching composition further comprises from 15% to 35% by weight of at least one inert organic liquid.

As used herein, the term "liquid" means a compound or a mixture of compounds that is liquid at 25° C. and at atmospheric pressure.

For example, the at least one inert organic liquid can be chosen from polydecenes, carboxylic acid monoesters and polyesters, sugar monoesters and polyesters of $C_8$–$C_{30}$ acids, cyclic ethers, cyclic esters, silicone oils, mineral oils and plant oils.

For instance, the polydecenes may be chosen from compounds of formula $C_{10n}H_{[(20n)+2]}$ wherein n is an integer ranging from 3 to 9, such as from 3 to 7. These compounds correspond to the name "polydecene" of the CTFA Dictionary 7th edition 1997, of the Cosmetics, Toiletry and Fragrance Association, USA, and also to the same INCI name in the USA and in Europe. They are poly-1-decene hydrogenation products.

Non-limiting examples of polydecanes that may be used include the product sold under the name Silkflo® 366 NF Polydecene by the company Amoco Chemical and those sold under the name Nexbase® 2002 FG, 2004 FG, 2006 FG and 2008 FG by the company Fortum.

As used herein, the carboxylic acid monoesters and polyesters, include: linear and branched, and saturated and unsaturated esters, they may, for example, comprise at least one $C_8$–$C_{30}$ hydrocarbon-based chain, further, for example, at least one $C_8$–$C_{24}$ hydrocarbon-based chain, such as at least one $C_{12}$–$C_{24}$ hydrocarbon-based chain, which may be derived from the acid and alcohol portion. The carboxylic acid monoesters and polyesters may also comprise at least one $C_1$–$C_8$ hydrocarbon-based chain and, for example, at least one $C_1$–$C_6$ hydrocarbon-based chain. In one embodiment, if the carboxylic acid comprises several carboxylic functional groups, these functional groups may, for example, all be esterified. It should be noted that the alcohols may, for example, be monofunctional alcohols.

Examples of esters include esters of oleic acid, lauric acid, palmitic acid, myristic acid, behenic acid, stearic acid, linoleic acid, linolenic acid, capric acid, and arachidonic acid, and mixtures thereof, such as oleo-palmitic, oleo-stearic, and palmito-stearic.

Furthermore, non-limiting examples include isopropyl diesters of sebacic acid (such as diisopropyl sebacate), dioctyl adipates and dicaprylyl maleates.

In one embodiment, it may be possible to use a polyester of a polycarboxylic acid comprising at least one group chosen from saturated and unsaturated, linear and branched groups comprising less than 6 carbon atoms, and of an alcohol comprising at least one group chosen from saturated and unsaturated, linear and branched groups with less than 6 carbon atoms. An example of the polyester of a polycarboxylic acid is triethyl citrate.

In another embodiment, the esters may be chosen from esters obtained from $C_{12}$–$C_{24}$ acids, for example, comprising at least one carboxylic group, and from saturated, linear and branched $C_3$–$C_6$ monoalcohols.

In one embodiment, the at least one inert liquid of the at least one anhydrous bleaching composition is chosen from isopropyl palmitate and isopropyl myristate, alone or as mixtures.

With regard to the sugar monoesters and polyesters of $C_8$–$C_{30}$ acids, such as $C_{12}$–$C_{24}$ acids, it is pointed out that the term "sugar" means compounds comprising several hydroxyl functional groups, with or without an aldehyde or ketone functional groups, and which comprise at least 4 carbon atoms. These sugars may be chosen, for example, from monosaccharides, oligosaccharides and polysaccharides. Non-limiting examples of suitable sugars include sucrose (and saccharose), glucose, galactose, ribose, fucose, maltose, fructose, mannose, arabinose, xylose and lactose, and derivatives thereof, for example, alkyl derivatives, such as methyl derivatives, for instance, methylglucose.

Examples of the saturated and unsaturated, linear and branched $C_8$–$C_{30}$ acids, comprising one and two carboxylic functional groups, include, as mentioned above, esters of oleic acid, lauric acid, palmitic acid, myristic acid, behenic acid, stearic acid, linoleic acid, linolenic acid, capric acid, and arachidonic acid, and mixtures thereof, such as oleo-palmitic, oleo-stearic, and palmito-stearic, isopropyl diesters of sebacic acid (such as diisopropyl sebacate), dioctyl adipates and dicaprylyl maleates, triethyl citrate, and acids of sugars, such as sucrose (and saccharose), glucose, galactose, ribose, fucose, maltose, fructose, mannose, arabinose, xylose and lactose, and derivatives thereof, for example, alkyl derivatives, such as methyl derivatives, for instance, methylglucose.

The esters may, for example, be chosen from monoesters, diesters, triesters, tetraesters and polyesters.

For example, the esters may be chosen from monoesters and diesters, such as saccharose, glucose and methylglucose monooleates, monostearates, monobehenates, monooleopalmitates, monolinoleates, monolinolenates, monooleostearates dioleates, distearates, dibehenates, dioleopalmitates, dilinoleates, dilinolenates and dioleostearates.

Non-limiting examples of the monoesters and diesters include the product sold under the name Glucate DO by the company Amerchol, which is a methylglucose dioleate; the products sold under the names F160, F140, F110, F90, F70 and SL40 by the company Crodesta, respectively denoting sucrose palmitostearates formed of 73% monoester and 27% diester and triester, 61% monoester and 39% diester, triester and tetraester, 52% monoester and 48% diester, triester and tetraester, 45% monoester and 55% diester, triester and tetraester, 39% monoester and 61% diester, triester and tetraester, and sucrose monolaurate; the products sold under the name Ryoto Sugar Esters, for example referenced B370 and corresponding to sucrose behenate formed of 20% monoester and 80% di-triester-polyester; sucrose mono-di-palmitostearate sold by the company Goldschmidt under the name Tegosoft PSE.

With regard to the cyclic esters and ethers, non-limiting examples include γ-butyrolactone, dimethyl isosorbide (CTFA name), and diisopropyl isosorbide (CTFA name).

The at least one inert liquid may be chosen, for example, from silicone oils, with a viscosity of less than or equal to 10 000 mPa·s at 25° C., the viscosity of the silicones being measured according to ASTM standard 445 Appendix C.

Silicone oils are defined in greater detail in Walter Noll's "Chemistry and Technology of Silicones" (1968)—Academic Press.

Suitable silicone oils include, for example, the silicone oils sold under the names DC-200 Fluid-5 mPa·s, DC-200 Fluid-20 mPa·s, DC-200 Fluid-350 mPa·s, DC-200 Fluid-1 000 mPa·s and DC-200 Fluid-10 000 mPa·s by the company Dow Corning.

In one embodiment the at least one inert liquid is a mineral oil, such as liquid paraffin.

Other examples include plant oils, such as avocado oil, olive oil and liquid jojoba wax.

Additives

Amphiphilic Polymers:

In one embodiment, the at least one anhydrous bleaching composition may further comprise common additives, such as amphiphilic polymers comprising at least one hydrophobic chain. As used herein, the term "amphiphilic polymer" means that the said polymer comprises both a hydrophilic portion and a hydrophobic portion, for example, a hydrophobic chain. Examples of the at least one amphiphilic polymer include nonionic, anionic, cationic and amphoteric amphiphilic polymers. In one embodiment, the at least one amphiphilic polymer is of nonionic, anionic or cationic nature.

It should be noted that the at least one amphiphilic polymer present in the at least one anhydrous bleaching composition and the at least one copolymer present in the at least one oxidizing composition, which will be described in detail later, may be different.

For example, the at least one amphiphilic polymer may comprise, as at least one hydrophobic chain chosen from, saturated and unsaturated, aromatic and non-aromatic, linear and branched $C_8$–$C_{30}$ hydrocarbon-based chains, and optionally comprising at least one oxyalkylene (such as oxyethylene and oxypropylene) unit.

The cationic amphiphilic polymers comprising the at least one hydrophobic chain may, for example, be chosen from cationic polyurethanes and cationic copolymers comprising at least one vinyllactam unit, such as vinylpyrrolidone units.

Even further, for example, the at least one amphiphilic polymers comprising at least one hydrophobic chain may be chosen from nonionic amphiphilic polymers comprising at least one hydrophobic chain and anionic amphiphilic polymers comprising at least one hydrophobic chain.

For example, the nonionic amphiphilic polymers comprising at least one hydrophobic chain, may be chosen from:

(1) celluloses modified with groups comprising at least one hydrocarbon-based chain chosen from saturated and unsaturated, linear and branched $C_6$–$C_{30}$ hydrocarbon-based chains, for instance, hydroxyethylcelluloses modified with groups comprising at least one hydrophobic chain as defined previously, such as Natrosol Plus Grade 330 CS($C_{16}$ alkyl—sold by the company Aqualon); Bermocoll EHM 100 (sold by the company Berol Nobel), Amercell Polymer HM-1500 (hydroxyethylcellulose modified with a polyethylene glycol (15) nonylphenyl ether group—sold by the company Amerchol).

(2) hydroxypropylguars modified with groups comprising at least one hydrophobic chain as defined above, for example Jaguar XC-95/3 ($C_{14}$ alkyl chain—sold by the company Rhodia Chimie); Esaflor HM 22 (C22 alkyl chain—sold by the company Lamberti); RE210-18 ($C_{14}$ alkyl chain) and RE205-1 ($C_{20}$ alkyl chain) sold by the company Rhodia Chimie.

(3) copolymers of vinylpyrrolidone and of hydrophobic monomers comprising at least one hydrophobic chain as defined above, for instance, Antaron and Ganex V216 (vinylpyrrolidone/hexadecene copolymers); Antaron and Ganex V220 (vinylpyrrolidone/eicosene copolymers), sold by the company I.S.P.

(4) copolymers of $C_1$–$C_6$ alkyl (meth)acrylates and of amphiphilic monomers comprising at least one hydrophobic chain.

(5) copolymers of hydrophilic (meth)acrylates and of hydrophobic monomers comprising at least one hydrophobic chain, for instance, a polyethylene glycol methacrylate/ lauryl methacrylate copolymer.

(6) polymers with an aminoplast ether skeleton comprising at least one fatty chain, such as the Pure Thix compounds sold by the company Süd-Chemie.

(7) linear (block structure), grafted and starburst polyurethanepolyethers comprising in their chain at least one hydrophilic block, which is generally a polyoxyethylene block which may comprise from 50 to 1 000 oxyethylene units, and at least one hydrophobic block, which may comprise aliphatic groups alone, optionally combined with cycloaliphatic and/or aromatic sequences. For example, the polyurethanepolyethers may comprise at least two $C_6$–$C_{30}$ hydrocarbon-based hydrophobic chains, separated by the at least one hydrophilic block; the hydrophobic chains may be pendent chains or chains with at least one of the end groups of the at least one hydrophilic block.

The polyurethanepolyethers may comprise a urethane bond between the at least one hydrophilic block. By extension, polyurethanepolyethers wherein the at least one hydrophilic block is linked to lipophilic blocks via other chemical bonds are also included.

The polyurethanepolyethers that may be used in the compositions disclosed herein include those described in the article by G. Fonnum, J. Bakke and Fk. Hansen—Colloid Polym. Sci. 271, 380.389 (1993). Further examples of polyurethanepolyethers that may be mentioned include Nuvis FX 1100 (European and US INCI name "Steareth-100/PEG-136/HMDI Copolymer" sold by the company Servo Delden); Rhéolate 205, 208, 204 and 212 (sold by the company Rheox); Elfacos T210 (C12–C14 alkyl chain) and Elfacos T212 (C18 alkyl chain) sold by the company Akzo.

In one embodiment, the at least one hydrophobic chain of the anionic amphiphilic polymers may be chosen from saturated and unsaturated, aromatic and non-aromatic, linear and branched $C_8$–$C_{30}$ hydrocarbon-based chains.

In one embodiment, the anionic amphiphilic polymers comprising at least one hydrophobic chain that may be used in the compositions disclosed herein, which may be crosslinked or non-crosslinked. They may also comprise at least one hydrophilic unit derived from at least one ethylenically unsaturated monomer bearing a free, partially or totally neutralized carboxylic acid functional group, and at least one hydrophobic unit derived from at least one ethylenically unsaturated monomer bearing at least one hydrophobic side chain, and optionally at least one crosslinking unit derived from at least one polyunsaturated monomer.

The at least one ethylenically unsaturated monomer bearing a carboxylic acid functional group may be chosen, for example, from ethacrylic acid, methacrylic acid and acrylic acid.

The at least one ethylenically unsaturated monomers bearing at least one hydrophobic side chain may, for example, be chosen from esters of unsaturated carboxylic acids, such as ethacrylic acid, methacrylic acid and acrylic acid, and saturated, linear and branched, $C_{10}$–$C_{30}$ alcohols, such as $C_{12}$–$C_{22}$ alcohols. The at least one ethylenically unsaturated monomers bearing at least one hydrophobic side chain may also be chosen from allylic ethers of saturated and unsaturated, aromatic and non-aromatic, branched and unbranched $C_6$–$C_{30}$ alcohols, which are optionally oxyalkylenated, for example, oxyethylenated, further, for example, from monomers of formula $CH_2$=CR'CH$_2$OB$_n$R wherein R' is chosen from H and CH$_3$, B is ethylenoxy, n is an integer ranging from 0 to 100, R is a hydrocarbon-based group chosen from alkyl, arylalkyl, aryl, alkylaryl and cycloalkyl groups comprising from 8 to 30 carbon atoms. For example, the unit may be such that R' is hydrogen, n is equal to 10 and R is a stearyl ($C_{18}$) group.

In one embodiment, the at least one crosslinking monomer, this monomer may comprise at least two polymerizable double bonds that are not conjugated with each other. For example, the at least one crosslinking monomer may be chosen from diallylphthalate, allyl (meth)acrylate, divinylbenzene, (poly)ethylene glycol dimethacrylate, methylenebisacrylamide, polyallylsucrose and polyallylpentaerythritol.

Anionic amphiphilic polymers of the type described above are described and prepared, for example, in U.S. Pat. Nos. 3,915,921 and 4,509,949 (copolymers of (meth)acrylic acid and of $C_{10}$–$C_{30}$ alkyl (meth)acrylates) or in Patent No. EP 216 479 (copolymers of (meth)acrylic acid and of fatty alkyl allyl ethers).

Examples of the amphiphilic polymers of the type described above include Carbopol ETD 2020 (acrylic acid/$C_{10}$–$C_{30}$ alkyl methacrylate crosslinked copolymer—sold by the company Goodrich); Carbopol 1382, Pemulen TR1 and Pemulen TR2 (acrylic acid/$C_{10}$–$C_{30}$ alkyl acrylate crosslinked copolymers—sold by the company Goodrich); oxyethylenated methacrylic acid/ethyl acrylate/stearyl methacrylate copolymer (55/35/10); oxyethylenated (25 EO) (meth)acrylic acid/ethyl acrylate/behenyl methacrylate copolymer and methacrylic acid/ethyl acrylate/steareth-10 allyl ether crosslinked copolymer.

In one embodiment, amphiphilic polymers used in the composition disclosed herein, are present in an amount ranging from 0.01% to 30% by weight, relative to the total weight of the composition. Water-soluble thickening polymers not comprising a hydrophobic chain:

In one embodiment, the at least one anhydrous bleaching composition may further comprise at least one water-soluble thickening polymer not comprising a hydrophobic chain.

The at least one water-soluble thickening polymer may, for example, be chosen from polymers of natural origin and synthetic polymers, and, further, for example, be chosen from those conventionally used in cosmetics. In addition, the at least one water-soluble thickening polymer does not contain a hydrophobic chain, i.e. hydrophobic chains chosen from saturated and unsaturated, aromatic and non-aromatic, linear and branched $C_8$–$C_{30}$ hydrocarbon-based chains, optionally comprising at least one oxyalkylene (oxyethylene and/or oxypropylene) unit.

Non-limiting examples of these polymers include: polyvinylpyrrolidone, polyacrylic acid, polyacrylamide, non-crosslinked poly(2-acrylamidopropanesulphonic acid) (Simugel EG from the company SEPPIC), crosslinked poly (2-acrylamido-2-methylpropanesulphonic acid), free and partially neutralized with ammonia (Hostacerin AMPS from Clariant), mixtures of non-crosslinked poly(2-acrylamido-2-methylpropanesulphonic acid) with hydroxyalkylcellulose ethers and with poly(ethylene oxides), as described in U.S. Pat. No. 4,540,510; mixtures of poly((meth)acrylamido ($C_1$–$C_4$)alkylsulphonic acid), which may, for example, be crosslinked, with a crosslinked copolymer of maleic anhydride and a ($C_1$–$C_5$)alkyl vinyl ether (Hostacerin AMPS/Stabileze QM from the company ISF).

The water-soluble thickening polymers of natural origin may, for example, be chosen from polymers comprising at least one sugar unit, for example, nonionic guar gums, optionally modified with at least one $C_1$–$C_6$ hydroxyalkyl group; biopolysaccharide gums of microbial origin, such as scleroglucan gum and xanthan gum; gums derived from plant exudates, such as gum arabic, ghatti gum, karaya gum, gum tragacanth, carrageenan gum, agar gum and carob gum; pectins; alginates; starches; hydroxy($C_1$–$C_6$)alkylcelluloses and carboxy($C_1$–$C_6$)alkylcelluloses.

As used herein, the term "sugar unit" means a monosaccharide (i.e. monosaccharide or oside or simple sugar) portion, an oligosaccharide portion (short chains formed from a sequence of monosaccharide units, which may be different) or a polysaccharide portion [long chains consisting of monosaccharide units, which may be different, i.e. polyholosides or polyosides]. The saccharide units may also be substituted with at least one substituent chosen from alkyl, hydroxyalkyl, alkoxy, acyloxy and carboxyl groups, the alkyl groups comprising from 1 to 4 carbon atoms.

Examples of nonionic, unmodified guar gums include Guargel D/15 (Goodrich); Vidogum GH 175 (Unipectine), Maypro-Guar 50 and Jaguar C (Meyhall/Rhodia Chimie); and examples of the modified nonionic guar gums include Jaguar HP8, HP60, HP120, DC 293 and HP 105 (Meyhall/Rhodia Chimie); Galactasol 4H4FD2 (Aqualon).

Examples of biopolysaccharide gums of microbial or plant origin are well known to those of ordinary skill in the art and are described, for example, in the book by Robert L. Davidson entitled "Handbook of Water soluble gums and resins" published by McGraw Hill Book Company (1980).

Non-limiting examples of these gums include scleroglucans, such as Actigum CS from Sanofi Bio Industries; Amigel from Alban Muller International, and also the glyoxal-treated scleroglucans described in Patent No. FR 2 633 940); xanthan gums, for example, Keltrol, Keltrol T, Keltrol Tf, Keltrol Bt, Keltrol Rd, Keltrol Cg (Nutrasweet Kelco), Rhodicare S and Rhodicare H (Rhodia Chimie); starch derivatives, for example, Primogel (Avebe); hydroxyethylcelluloses, such as Cellosize QP3L, QP4400H, QP30000H, HEC30000A and Polymer PCG10 (Amerchol), Natrosol 250HHR, 250MR, 250M, 250HHXR, 250HHX, 250HR, HX (Hercules) and Tylose H1000 (Hoechst); hydroxypropylcelluloses, for example, Klucel EF, H, LHF, MF and G (Aqualon); carboxymethylcelluloses, such as Blanose 7M8/SF, refined 7M, 7LF, 7MF, 9M31 F, 12M31XP, 12M31P, 9M31XF, 7H, 7M31, 7H3SXF (Aqualon), Aquasorb A500 (Hercules), Ambergum 1221 (Hercules), Cellogen HP810A, HP6HS9 (Montello) and Primellose (Avebe).

In one embodiment, the at least one water-soluble thickening polymers not comprising a hydrophobic chain, are present in an amount ranging from 0.01% to 30% by weight, relative to the total weight of the at least one anhydrous bleaching composition.

Surfactants:

The at least one anhydrous bleaching composition may also comprise at least one surfactant chosen from anionic, nonionic, cationic, amphoteric and zwitterionic surfactants.

Non-limiting examples of the anionic surfactants that can be used in the compositions disclosed herein include salts (for example, alkali metal salts, such as sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates and ($C_6$–$C_{24}$)acyl glutamates. It is also possible to use ($C_6$–$C_{24}$)alkylpolyglycoside carboxylic esters, such as alkylglycoside citrates, alkylglycoside tartrates and alkylglycoside sulphosuccinates, alkylsulphosuccinamates; acyl isethionates and N-acyl taurates, wherein the alkyl and acyl groups of all of these different compounds, for example, comprises from 12 to 20 carbon atoms and the aryl group may, for example, be chosen from phenyl and benzyl groups. Among the anionic surfactants which can also be used, non-limiting mention may be made of fatty acid salts (for example, $C_6$–$C_{24}$ acid salts), such as oleic, ricinoleic and palmitic acid salts, coconut oil acid and hydrogenated coconut oil acid, and, for example, sodium, calcium and magnesium salts of stearic acid; acyl lactylates wherein the acyl group comprises from 8 to 20 carbon atoms. It is also possible to use alkyl D-galactoside uronic acids and their salts, polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, for example those comprising from 2 to 50 alkylene oxide groups, such as ethylene oxide groups, and mixtures thereof.

Without wishing to be limited thereto, the nonionic surfactants may also be chosen, for example from polyethoxylated and polypropoxylated, alkylphenols, alpha-diols and alcohols, comprising at least one chain comprising, for example, from 6 to 24 carbon atoms, and further, for example, from 8 to 22 carbon atoms, it being possible for the number of ethylene oxide and/or propylene oxide groups to range, for example, from 1 to 50. Further examples also include copolymers of ethylene oxide and of propylene oxide, condensates of ethylene oxide and of propylene oxide with fatty alcohols (for example, $C_6$–$C_{24}$); polyethoxylated fatty amides (for example, $C_6$–$C_{24}$) for example, comprising from 2 to 30 mol of ethylene oxide, monoglycerolated and polyglycerolated fatty alcohols (for example, $C_6$–$C_{24}$) comprising, for example, from 1 to 30 glycerol groups and polyglycerolated fatty amides (for example, $C_6$–$C_{24}$) comprising, for example, from 1 to 5 glycerol groups, and, further, for example, from 1.5 to 4, glycerol groups; oxyethylenated fatty acid esters (for example, $C_6$–$C_{24}$) of sorbitan comprising, for example, from 2 to 30 mol of ethylene oxide; fatty acid esters (for example, $C_6$–$C_{24}$) of sucrose, fatty acid esters (for example, $C_6$–$C_{24}$) of polyethylene glycol, alkylpolyglycosides, N-alkylglucamine derivatives, and amine oxides, such as ($C_{10}$–$C_{14}$)alkylamine oxides and N-acylaminopropyl-morpholine oxides.

For example, the amphoteric or zwitterionic surfactants may chosen from aliphatic secondary and tertiary amine derivatives wherein the aliphatic group is chosen from linear and branched $C_8$–$C_{18}$ chains comprising at least one anionic group chosen from carboxylate, sulphonate, sulphate, phosphate and phosphonate groups; ($C_8$–$C_{20}$)alkylbetaines, ($C_8$–$C_{20}$)alkylsulphobetaines, ($C_8$–$C_{20}$)alkylamido($C_1$–$C_6$) alkylbetaines and ($C_8$–$C_{20}$)alkylamido($C_1$–$C_6$)alkylsulphobetaines. Further examples include ampho-carboxyglycinates and ampho-carboxypropionates, classified in the CTFA dictionary, 5th edition, 1993, under the names Disodium Cocoamphodiacetate, Disodium Lauroamphodiacetate, Disodium Caprylamphodiacetate, Disodium Caprylo amphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid. For example, mention may be made of Cocoamphodiacetate (Miranol® C2M Concentrate from Rhodia Chimie).

The cationic surfactants may, for example, be chosen from salts of optionally polyoxyalkylenated primary, secondary and tertiary fatty amines; quaternary ammonium salts, such as tetraalkylammonium, alkylamidoalkyltrialkylammonium, trialkylbenzylammonium, trialkylhydroxyalkylammonium or alkylpyridinium chlorides and bromides; imidazoline derivatives; and amine oxides of cationic nature.

For example, when the at least one surfactant is present, if may be chosen from anionic and nonionic compounds.

In one embodiment, the at least one surfactant is present in the at least one anhydrous bleaching composition, its content is such that the total surfactant content in the ready-to-use composition ranges, for example, from 0.05% to 30% by weight, and, further, for example from 0.1% to 20% by weight.

Cationic and Amphoteric Substantive Polymer:

In one embodiment, the at least one anhydrous bleaching composition comprises at least one substantive polymer chosen from cationic and amphoteric substantive polymers. Polymers of this type may, for example, make it possible to improve the cosmetic properties of the fibers (conditioning effect).

As used herein, the expression "cationic polymer" means any polymer comprising at least one group chosen from cationic groups and groups that may be ionized into cationic groups.

The cationic and amphoteric polymers that may, for example, be used in the compositions disclosed herein may be chosen from those already known per se as improving the cosmetic properties of the hair, i.e. those described in the Patents and Patent Applications Nos. EP 337 354, FR 2 270 846, FR 2 383 660, FR 2 598 611, FR 2 470 596, FR 2 519 863, FR 2 788 974 and FR 2 788 976 for a list of these compounds.

The cationic polymers may, for example, be chosen from cationic polymers comprising at least one group chosen from primary, secondary, tertiary and quaternary amine groups, which may either form part of the main polymer chain and may be borne by a side substituent directly attached to the main polymer chain.

Further non-limiting examples of the cationic polymers include:

(1) copolymers of acrylamide and of dimethylaminoethyl methacrylate quaternized with dimethyl sulphate and with a dimethyl halide (Hercofloc from Hercules); copolymers of acrylamide and of methacryloyloxyethyltrimethylammonium chloride (Bina Quat P 100 from Ciba Geigy); copolymers of acrylamide and of methacryloyloxyethyltrimethylammonium methosulphate (Reten from Hercules); quaternized and non-quaternized vinylpyrrolidone/dialkylaminoalkyl acrylate and methacrylate copolymers (Gafquat range from ISP; Copolymer 845, 958 and 937 from Gaf Corporation (ISP)); dimethylaminoethyl methacrylate/vinylcaprolactam/vinylpyrrolidone terpolymers (Gaffix VC 713 from ISP); vinylpyrrolidone/methacrylamidopropyl-dimethylamine copolymers (Styleze CC 10 from ISP); vinylpyrrolidone/dimethylaminopropylmethacrylamide quaternized copolymers (Gafquat HS 100 from ISP).

(2) Cellulose ether derivatives comprising quaternary ammonium groups, as described in Patent No. FR 1 492 597. These polymers are also defined in the CTFA dictionary as quaternary ammoniums of hydroxyethylcellulose which has reacted with an epoxide substituted with a trimethylammonium group.

(3) Cationic cellulose derivatives, such as copolymers of cellulose and cellulose derivatives grafted with a water-soluble quaternary ammonium monomer, described, for example, in U.S. Pat. No. 4,131,576, such as hydroxyalkylcelluloses, for instance, hydroxymethylcellulose, hydroxyethylcellulose and hydroxypropylcellulose grafted, for example with a salt chosen from methacryloylethyltrimethylammonium, methacrylamidopropyltrimethylammonium and dimethyldiallylammonium salts.

(4) The cationic polysaccharides described more, for example, in U.S. Pat. Nos. 3,589,578 and 4,031,307, such as guar gums comprising trialkylammonium cationic groups. Guar gums modified with a salt, such as chloride. For example, guar gums modified with a salt of 2,3-epoxypropyltrimethylammonium chloride may be used.

(5) Polymers comprising piperazinyl units and divalent alkylene and hydroxyalkylene groups comprising straight and branched chains, optionally interrupted with at least one entity chosen from oxygen, sulphur and nitrogen and aromatic and heterocyclic groups, and also the oxidation and quaternization products of these polymers. Such polymers are described, for example, in Patent Nos. FR 2 162 025 and FR 2 280 361.

(6) Water-soluble polyaminoamides prepared, for example, by polycondensation of an acidic compound with a polyamine, which are optionally crosslinked, optionally alkylated, or, if they comprise at least one tertiary amine functional group, quaternized. These polymers are described, for example, in Patent Nos. FR 2 252 840 and FR 2 368 508.

(7) Polyaminoamide derivatives resulting from the condensation of polyalkylene polyamines with polycarboxylic acids followed by an alkylation with difunctional agents. Examples of these polyaminoamide derivatives include adipic acid-dialkylaminohydroxyalkyldialkylene-triamine polymers wherein the alkyl group is $C_1$–$C_4$. Such polymers are described, for example, in Patent No. FR 1 583 363.

(8) Polymers obtained by reacting a polyalkylene polyamine comprising two primary amine groups and at least one secondary amine group with a dicarboxylic acid chosen from diglycolic acid and saturated $C_3$–$C_8$ aliphatic dicarboxylic acids, and then with epichlorohydrin. Such polymers are described, for example, in U.S. Pat. Nos. 3,227,615 and 2,961,347.

(9) Cyclopolymers of alkyldiallylamine and of dialkyldiallylammonium, in homopolymer or copolymer form, as described in Patent No. FR 2 080 759 and in its Certificate of Addition No. 2 190 406.

(10) Diquaternary ammonium polymers as described in Patent Nos. FR 2 320 330, FR 2 270846, FR 2316271, FR 2 336434, FR 2413907, U.S. Pat. No. 2,273,780, U.S. Pat. No. 2,375,853, U.S. Pat. No. 2,388,614, U.S. Pat. No. 2,454,547, U.S. Pat. No. 3,206,462, U.S. Pat. No. 2,261,002, U.S. Pat. No. 2,271,378, U.S. Pat. No. 3,874,870, U.S. Pat. No. 4,001,432, U.S. Pat. No. 3,929,990, U.S. Pat. No. 3,966,904, U.S. Pat. No. 4,005,193, U.S. Pat. No. 4,025,617, U.S. Pat. No. 4,025,627, U.S. Pat. No. 4,025,653, U.S. Pat. No. 4,026,945 and U.S. Pat. No. 4,027,020.

Examples of these polymers, used as disclosed herein, comprise repeating units corresponding to the following formula:

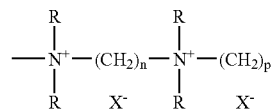

wherein R, which may be identical or different, is chosen from $C_1$–$C_4$ alkyl and hydroxyalkyl; n and p, which may be identical or different, are integers ranging from 2 to 20; and X— is an anion chosen from anions derived from mineral and organic acids.

(11) Poly(quaternary ammonium) polymers comprising repeating units of formula:

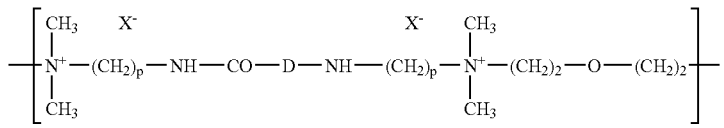

wherein p is an integer ranging from 1 to 6, D may be nothing or may represent a group —(CH2)r-CO— wherein r is an integer equal to 4 or 7, and X— is an anion. Such polymers may be prepared according to the processes described in Patent Nos. U.S. Pat. No. 4,157,388, U.S. Pat. No. 4,702,906, U.S. Pat. No. 4,719,282 and EP 122 324.

(12) Quaternary polymers of vinylpyrrolidone and of vinylimidazole.

(13) Polyamines of the polyethylene glycol (15) tallow polyamine type (CTFA dictionary name).

(14) Crosslinked methacryloyloxy($C_1$–$C_4$)alkyltri($C_1$–$C_4$) alkylammonium salt polymers, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, for example, methylenebisacrylamide. A crosslinked acrylamide/methacryloyloxyethyltrimethylammonium chloride copolymer (20/80 by weight) in the form of a dispersion comprising 50% by weight of the said copolymer in mineral oil can, for example, be used. This dispersion is sold under the name "Salcare® SC 92" by the company Allied Colloids. A crosslinked methacryloyloxyethyltrimethylammonium chloride homopolymer comprising about 50% by weight of the homopolymer in mineral oil or in a liquid ester can also be used. These dispersions are sold under the names "Salcare® SC 95" and "Salcare® SC 96" by the company Allied Colloids.

Further examples of cationic polymers that can be used in the compositions disclosed herein include polyalkyleneimines, such as polyethyleneimines, polymers comprising at least one unit chosen from vinylpyridine and vinylpyridinium units, condensates of polyamines and of epichlorohydrin, quaternary polyureylenes and chitin derivatives.

The amphoteric polymers may, for example, be chosen from polymers comprising units K and M randomly distributed in the polymer chain, wherein K is a unit derived from a monomer comprising at least one basic nitrogen atom and M is a unit derived from an acidic monomer comprising at least one carboxylic and sulphonic groups, or alternatively K and M, which may be identical or different, may be chosen from groups derived from zwitterionic carboxybetaine and sulphobetaine monomers;

K and M, which may be identical or different, may also be chosen from cationic polymer chains comprising at least one group chosen from primary, secondary, tertiary or quaternary amine groups, wherein at least one of the amine groups bears a carboxylic or sulphonic group linked via a hydrocarbon-based radical, or alternatively K and M, which may be identical or different, form part of a chain of a polymer comprising α,β-dicarboxylic ethylene units wherein one of the carboxylic groups has been made to react with a polyamine comprising at least one amine group chosen from primary or secondary amine groups.

The amphoteric polymers corresponding to the above definition may be chosen, for example, from the following polymers:

(1) Polymers resulting from the copolymerization of a monomer derived from a vinyl compound bearing a carboxylic group, such as acrylic acid, methacrylic acid, maleic acid, α-chloroacrylic acid, and a dialkyldiallylammonium salt, such as dimethyldiallylammonium chloride, and a basic monomer derived from a substituted vinyl compound comprising at least one basic atom, such as dialkylaminoalkyl methacrylate and acrylate, dialkylaminoalkylmethacrylamide and -acrylamide. Such compounds are described in U.S. Pat. No. 3,836,537. Mention may also be made of the sodium acrylate/acrylamidopropyltrimethylammonium chloride copolymer (Polyquart KE 3033 by the company Henkel) and the acrylic acid/dimethyldiallylammonium chloride copolymer (Merquat 280, 295, Plus 3330, from Calgon).

(2) Polymers comprising units derived from a) at least one monomer chosen from acrylamides and methacrylamides substituted on the nitrogen with an alkyl radical, for example, $C_2$–$C_{12}$ (such as ethyl, tert-butyl, tert-octyl, octyl, decyl and dodecyl), b) at least one acidic monomer comprising at least one reactive carboxylic group (for example, acrylic acid, methacrylic acid, crotonic acid and itaconic acid, and monoesters of maleic and fumaric acids and anhydrides), and c) at least one basic monomer, such as esters comprising at least one substituent chosen from primary, secondary, tertiary and quaternary amine substituents of acrylic acid, methacrylic acid, fumaric acid and maleic acid, and products of quaternization of dimethylaminoethyl methacrylate with dimethyl and diethyl sulphate (for example, aminoethyl, butylaminoethyl, N,N'-dimethylaminoethyl and N-tert-butylaminoethyl methacrylates).

Octylacrylamide/acrylate/butylaminoethyl methacrylate copolymers (Amphomer or Lovocryl 47 by the company National Starch) may, for example, be used.

(3) Crosslinked and partially or totally alkylated polyaminoamides, derived from polyaminoamides of general formula —[CO—R—CO-Z]- wherein R is chosen from divalent groups derived from saturated and unsaturated dicarboxylic acids (for example, adipic acid, 2,2,4-trimethyladipic acid, 2,4,4-trimethyladipic acid, terephthalic acid and itaconic acid), unsaturated monocarboxylic acids (for instance, (meth)acrylic acid), $C_1$–$C_6$ alkyl esters of the abovementioned acids and groups derived from the addition of one of these acids to a bis-primary or bis-secondary amine, and Z is chosen from groups of bis-primary, mono- and bis-secondary polyalkylenepolyamines. For example, Z represents:

(a) from 60 to 100 mol %, —NH—[($CH_2$)$_x$—NH]$_p$ wherein x=2 and p=2 or 3, or x=3 and p=2; and wherein the group is derived from diethylenetriamine, from triethylenetetramine and from dipropylenetriamine;

(b) from 0 to 40 mol %, wherein x=2 and p=1 and wherein the group is derived from ethylenediamine, or the group derived from piperazine —N[CH2CH2]2N—;
(c) from 0 to 20 mol %, —NH—(CH2)6-NH— derived from hexamethylenediamine. The crosslinking agent for these polymers is a difunctional agent chosen from epihalohydrins, diepoxides, dianhydrides and bis-unsaturated derivatives, and alkylated by the action of acrylic acid, chloroacetic acid and alkane sultone (for example, propane sultone and butane sultone) and the alkali metal salts thereof.
(4) Polymers comprising at least one zwitterionic unit, for example, the butyl methacrylate/dimethylcarboxymethylammonioethyl methacrylate copolymer (Diaformer Z301 from Sandoz).
(5) Polymers derived from chitosan comprising monomer units chosen from the following formulae (I), (II) and (III) below:

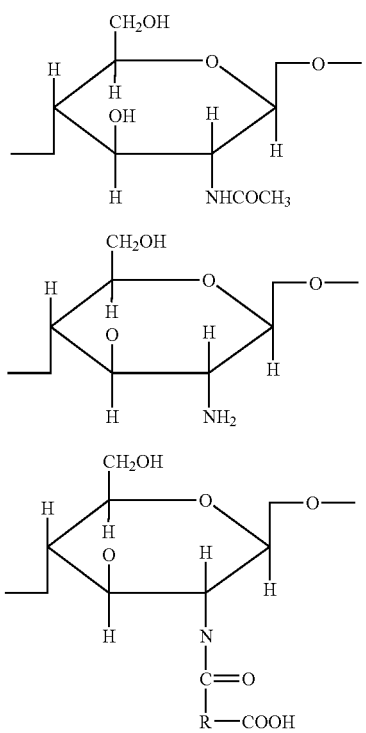

wherein unit (I) is present in an amount ranging from 0 to 30% by weight, relative to the total weight, unit (II) is present in an amount ranging from 5% to 50% by weight, relative to the total weight and unit (III) is present in an amount ranging from 30% to 90% by weight, relative to the total weight, wherein R is chosen from a group of formula:

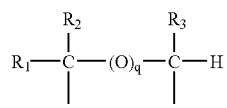

wherein q is equal to 0 or 1; and if q is equal to 0, then $R_1$, $R_2$, and $R_3$ which may be identical or different, are chosen from hydrogen, methyl, hydroxyl, acetoxy, amino, monoalkylamino and dialkylamino groups, optionally interrupted with at least one nitrogen and optionally substituted with at least one substituent chosen from amine, hydoxyl and carboxyl groups, alkylthio groups optionally bearing amino groups, and sulphonic groups; or, if q is equal to 1, then $R_1$, $R_2$, and $R_3$, which may be identical or different, are chosen from hydrogen and salts formed by these compounds with acids or bases.
(6) Polymers derived from the N-carboxyalkylation of chitosan, such as N-carboxymethyl-chitosan and N-carboxybutylchitosan (Evalsan from Jan Dekker).
(7) Polymers as described in French Patent No. 1 400 366:

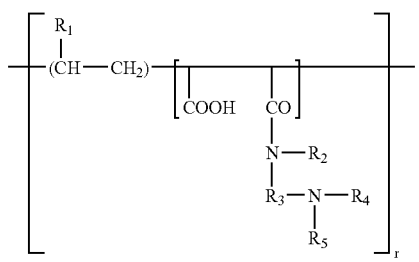

wherein $R_1$ is chosen from hydrogen, $CH_3O$—, $CH_3CH_2O$— and phenyl, $R_2$ and $R_5$, which may be identical or different, are chosen from hydrogen and alkyl groups (such as methyl and ethyl), $R_4$ is chosen from alkyl groups (such as methyl and ethyl) and groups of formula —$R_3$—$N(R_5)_2$, wherein $R_3$ is chosen from —$(CH_2)_2$—, —$(CH_2)_3$— and —$CH_2$—$CH(CH_3)$—, and also the higher homologues of these groups and comprising up to 6 carbon atoms, and r is chosen such that the molecular weight of the polymer ranges from 500 to 6 000 000, such as from 1 000 to 1 000 000.
(8) Amphoteric polymers of the type -D-X-D-X- chosen from:
a) polymers obtained by the action of chloroacetic acid or sodium chloroacetate on compounds comprising at least one unit of formula -D-X-D-X-D- wherein D is —N[CH$_2$CH$_2$]$_2$N— (piperazinyl) and X is chosen from symbols E and E', wherein E and E', which may be identical or different, may be chosen from divalent alkylene groups comprising at least one chain chosen from straight and branched chains comprising up to 7 carbon atoms in the main chain, wherein the divalent alkylene groups are optionally substituted with at least one hydroxyl group and possibly further also comprising at least one entity chosen from oxygen, nitrogen and sulphur, and from 1 to 3 aromatic and heterocyclic rings; wherein the oxygen, nitrogen and sulphur atoms can be present in the form of at least one group chosen from ether, thioether, sulphoxide, sulphone, sulphonium, alkylamine and alkenylamine groups, hydroxyl, benzylamine, amine oxide, quaternary ammonium, amide, imide, alcohol, ester and urethane groups;
b) polymers of formula -D-X-D-X- wherein D is —N[CH$_2$CH$_2$]$_2$N— (piperazinyl) and X is chosen from symbols E and E' and at least once is chosen from E'; wherein E has the meaning defined above and E' is chosen from divalent alkylene groups comprising at least one chain chosen from straight and branched chains comprising up to 7 carbon atoms in the main chain, wherein the divalent alkylene groups are optionally substituted with at least one hydroxyl group and comprising at least one nitrogen, wherein the nitrogen atom is substituted with an alkyl chain, which is optionally interrupted by an oxygen atom and wherein the divalent aklylene groups comprise at least one functional group chosen from carboxyl and hydroxyl functional groups and wherein the alkyl chain can be betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine, such as N,N-dimethylamino-propylamine or by semiesterification with an N,N-dialkanolamine. These copolymers can further comprise other vinyl comonomers, such as vinylcaprolactam.

Among all the cationic and amphoteric polymers that may be used, in the composition disclosed herein, non-limiting examples include:

(i) among the cationic polymers:
dimethyldiallylammonium chloride homopolymers (Merquat 100 DRY from Nalco);
copolymers of dimethyldiallylammonium chloride and of acrylamide (Merquat 2200 from Nalco);
Polymers of poly(quaternary ammonium) prepared and described in French Patent No. 2 270 846, comprising repeating units chosen from units of formulae (W) and (U) below:

$$-\left[N^+(CH_3)_2-(CH_2)_3-N^+(CH_3)_2-(CH_2)_6\right]- \quad 2Cl^- \tag{W}$$

and, for example, those polymers comprising repeating units of formula (W) with a molecular weight, determined by gel permeation chromatography, ranging from 9 500 to 9 900;

$$-\left[N^+(CH_3)_2-(CH_2)_3-N^+(C_2H_5)_2-(CH_2)_3\right]- \quad 2Br^- \tag{U}$$

and, for example, those polymers comprising repeating units of formula (U) with a molecular weight, determined by gel permeation chromatography, of about 1 200;

polymers of poly(quaternary ammonium) of family (11) wherein X— is chlorine, and, for example, those polymers with a weight-average molecular mass of less than 100 000 and, for example, less than or equal to 50 000;

(ii) among the amphoteric polymers:
dimethyldiallylammonium chloride/acrylic acid copolyer (80/20) (Merquat 280 Dry from Calgon—CTFA name: Polyquaternium 22);
dimethyldiallylammonium chloride/acrylic acid copolymer (95/5) (Merquat 295 Dry from Calgon);
methacrylamidopropyltrimonium chloride, acrylic acid and ethyl acrylate copolymer (Merquat 2001 from Calgon—CTFA name: Polyquaternium 47);
acrylamide/dimethyldiallylammonium chloride/acrylic acid terpolymer (Merquat Plus 3330 Dry from Calgon—CTFA name: Polyquaternium 39).

Other Additives

The at least one anhydrous bleaching composition may also comprise at least one mineral filler, for example, clays and silicas, such as fumed silicas of hydrophilic and hydrophobic nature.

It may also comprise at least one binder, such as vinylpyrrolidone, at least one lubricant, for instance, polyolstearates and alkali metal and alkaline-earth metal stearates, and also agents for controlling the release of oxygen, such as magnesium carbonate and magnesium oxide.

The at least one anhydrous bleaching composition may comprise, where appropriate, at least one agent chosen from dyes, mattifying agents, for example, titanium oxides, sequestering agents, vitamins and provitamins, sunscreens, silicones and fragrances.

In one embodiment, the at least one anhydrous bleaching composition in paste form may conventionally be prepared by dispersing, with mechanical stirring, all of the pulverulent compounds in the inert liquid, in which the other liquid compounds of the bleaching composition have previously been dispersed or mixed.

In one embodiment, the at least one anhydrous bleaching composition may also be prepared via extrusion, by introducing the liquid and solid phases of the composition into the extruder and then mixing them at a temperature below 25° C. using a co-rotating twin-screw system composed of transportation and blending members.

The oxidizing composition will now be described.

Oxidizing Composition

In one embodiment, the at least one oxidizing composition is a hydrogen peroxide oil-in-water emulsion comprising at least one surfactant chosen from nonionic and anionic surfactants and at least one copolymer obtained from at least one ethylenically unsaturated monomer comprising at least one sulphonic group, in free or partially or totally neutralized form and comprising at least one hydrophobic unit.

Surfactants

With regard to the nonionic and anionic surfactants, reference may be made to the lists detailed previously in the context of the description of the components comprising the at least one anhydrous bleaching composition.

For example, the at least one surfactant may be chosen from alkyl sulphates and alkyl ether sulphates of an alkali metal, such as sodium and potassium, of an alkaline-earth metal, for instance, magnesium, of ammonium, of amines and of amino alcohols.

Further, for example, at least one nonionic surfactant may be chosen from polyethoxylated and polypropoxylated fatty alcohols (such as $C_6$–$C_{24}$ alcohols), the number of ethylene oxide and/or propylene oxide groups may range, for example, from 1 to 50 groups; mono- and polyglycerolated fatty alcohols (such as $C_6$–$C_{24}$ alcohols) comprising, for example, from 1 to 30 glycerol groups, and polyglycerolated fatty amides (such as $C_6$–$C_{24}$ amides) comprising, for example, from 1 to 5 glycerol groups and, further, for example, from 1.5 to 4 glycerol groups.

In one embodiment, the at least one surfactant present in the at least one hydrogen peroxide oil-in-water emulsion is present in an amount ranging, for example, from 0.05% to 30% by weight, relative to the total weight of the at least one hydrogen peroxide oil-in-water emulsion and, further, for example, from 0.1% to 20% by weight, relative to the total weight of the at least one hydrogen peroxide oil-in-water emulsion.

For example, the ready-to-use composition, i.e. the at least one anhydrous bleaching composition and the at one oxidizing composition, may have a total surfactant content ranging, for example, from 0.05% to 30% by weight, relative to the total weight of the ready-to-use composition and, further, for example, from 0.1% to 20% by weight, relative to the total weight of the ready-to-use composition.

Copolymer

The at least one copolymer present in the at least one oxidizing composition comprises at least one unit derived from an ethylenically unsaturated monomer comprising at least one sulphonic group, in free form or partially or totally neutralized form, and comprising at least one hydrophobic portion.

The ethylenically unsaturated monomers comprising at least one sulphonic group can be chosen, for example, from vinylsulphonic acid, styrenesulphonic acid, (meth)acrylamido($C_1$–$C_{22}$)alkylsulphonic acids, and N-($C_1$–$C_{22}$)alkyl (meth)acrylamido($C_1$–$C_{22}$)alkylsulphonic acids, for instance, undecylacrylamidomethanesulphonic acid, and also partially or totally neutralized forms thereof.

(Meth)acrylamido($C_1$–$C_{22}$)alkylsulphonic acids, such as acrylamidomethanesulphonic acid, acrylamidoethanesulphonic acid, acrylamidopropanesulphonic acid, 2-acrylamido-2-methylpropanesulphonic acid, methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid and 2-acrylamido-2,6-dimethyl-3-heptanesulphonic acid, and also partially or totally neutralized forms thereof, can, for example, be used. For example, 2-acrylamido-2-methylpropanesulphonic acid (AMPS) and partially or totally neutralized forms thereof can be used.

The total or partial neutralization of the sulphonic functions of the copolymer may, for example, be performed using a mineral base, such as sodium hydroxide, potassium hydroxide or aqueous ammonia; or an organic base, such as mono-, di- or triethanolamine, an aminomethylpropanediol, N-methylglucamine, basic amino acids, for instance, arginine and lysine, and mixtures of these compounds.

The hydrophobic portion of the copolymer can, for example, comprise from 6 to 50 carbon atoms, further, for example, from 6 to 22 carbon atoms, and even further, for example, from 6 to 18 carbon atoms, such as from 12 to 18 carbon atoms.

In one embodiment, the copolymers disclosed herein are crosslinked.

The crosslinking agents may, for example, be chosen from polyolefinically unsaturated compounds commonly used for the crosslinking of polymers obtained by free-radical polymerization. Non-limiting mention may be made, for example, of divinylbenzene, diallyl ethers, dipropylene glycol diallyl ethers, polyglycol diallyl ethers, triethylene glycol divinyl ethers, hydroquinone diallyl ethers, ethylene glycol di(meth)acrylates and tetraethylene glycol di(meth) acrylates, trimethylolpropane triacrylates, methylenebisacrylamides, methylenebismethacrylamides, triallylamine, triallyl cyanurate, diallyl maleates, tetraallyl-ethylenediamines, tetraallyloxyethanes, trimethylolpropane diallyl ethers, allyl (meth)acrylates, allylic ethers of alcohols of the sugar series, and other allyl and vinyl ethers of polyfunctional alcohols, and also allylic esters of phosphoric and vinylphosphonic acid derivatives.

For example, methylenebisacrylamide, allyl methacrylate and trimethylolpropane triacrylate (TMPTA) can be used.

The degree of crosslinking, in the copolymer, may range, for example, from 0.01 mol % to 10 mol % relative to the copolymer and, further, for example, from 0.2 mol % to 2 mol % relative to the copolymer.

In one embodiment, the copolymers, as disclosed herein, have a number-average molecular weight ranging, for example, from $10^3$ g/mol to $2 \times 10^7$ g/mol, further, for example, from $2 \times 10^3$ g/mol to $5 \times 10^6$ g/mol and even further, for example, from $10^5$ g/mol to $15 \times 10^5$ g/mol.

The copolymers, as disclosed herein, may be chosen, for example, from random amphiphilic AMPS polymers modified by reaction with at least one $C_6$–$C_{22}$ n-monoalkylamine and di-n-alkylamine, such as those described in Patent Application No. WO 00/31154, the description of the polymers and of the synthesis of which forms part of the content of the description.

In one embodiment, the disclosed copolymers may also comprise other ethylenically unsaturated hydrophilic monomers chosen, for example, from (meth)acrylic acids, β-substituted alkyl derivatives thereof and esters thereof obtained with monoalcohols and mono- and polyalkylene glycols, (meth)acrylamides, vinylpyrrolidone, maleic anhydride, and itaconic acid and maleic acid.

For example, the copolymers disclosed herein are chosen from amphiphilic copolymers of AMPS and at least one ethylenically unsaturated hydrophobic monomer comprising at least one hydrophobic portion comprising from 6 to 50 carbon atoms, for example, from 6 to 22 carbon atoms, further, for example, from 6 to 18 carbon atoms and even further, for example, from 12 to 18 carbon atoms.

The disclosed copolymers may also comprise at least one ethylenically unsaturated monomer not comprising a fatty chain, such as (meth)acrylic acids, β-substituted alkyl derivatives thereof and esters thereof obtained with monoalcohols and mono- and polyalkylene glycols, (meth)acrylamides, vinylpyrrolidone, maleic anhydride, and itaconic acid and maleic acid.

Examples of copolymers are described in Patent Application No. EP-A-750 899, and Patent Nos. U.S. Pat. No. 5,089,578 and FR 2 818 543 and in the following publications from Yotaro Morishima:

"Self-assembling amphiphilic polyelectrolytes and their nanostructures—Chinese Journal of Polymer Science Vol. 18, No. 40, (2000), 323–336";

"Micelle formation of random copolymers of sodium 2-(acrylamido)-2-methylpropanesulphonate and a non-ionic surfactant macromonomer in water as studied by fluorescence and dynamic light scattering—Macromolecules 2000, Vol. 33, No. 10-3694–3704";

"Solution properties of micelle networks formed by nonionic moieties covalently bound to a polyelectrolyte: salt effects on rheological behavior—Langmuir, 2000, Vol. 16, No. 12, 5324–5332";

"Stimuli responsive amphiphilic copolymers of sodium 2-(acrylamido)-2-methylpropanesulphonate and associative macromonomers—Polym. Preprint, Div. Polym. Chem. 1999, 40(2), 220–221".

The ethylenically unsaturated hydrophobic monomers of the disclosed copolymers are chosen, for example, from acrylates and acrylamides of formula (I) below:

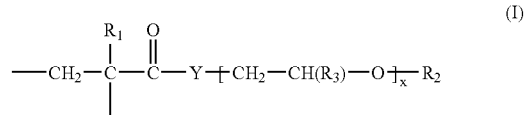

wherein $R_1$ and $R_3$, which may be identical or different, are chosen from hydrogen and linear and branched $C_1$–$C_6$ alkyl groups (such as methyl); Y is chosen from O and NH; $R_2$ is chosen from hydrophobic hydrocarbon-based groups comprising from 6 to 50 carbon atoms, for example, from 6 to 22 carbon atoms, further, for example, from 6 to 18 carbon atoms, and even further, for example, from 12 to 18 carbon atoms; x is an integer ranging from 0 to 100.

For example, $R_2$ is chosen from linear $C_6$–$C_{18}$ alkyl groups (for example, n-hexyl, n-octyl, n-decyl, n-hexadecyl and n-dodecyl) and branched and cyclic $C_6$–$C_{18}$ alkyl groups (for example, cyclododecane ($C_{12}$) and adamantane ($C_{10}$)); $C_6$–$C_{18}$ alkylperfluoro groups (for example, groups of formula —$(CH_2)_2$—$(CF_2)_9$—$CF_3$); cholesteryl groups ($C_{27}$) and cholesterol ester residues, for instance, cholesteryl oxyhexanoate groups; aromatic polycyclic groups, for instance, naphthalene and pyrene. Among these groups, $R_2$ can be chosen, for example, from linear alkyl groups and n-dodecyl groups.

In one embodiment, the monomer of formula (I) comprises at least one alkylene oxide unit ($x \geq 1$), such as polyoxyalkylenated chains. The polyoxyalkylenated chain can comprise, for example, at least one unit chosen from ethylene oxide and propylene oxide units, such as ethylene oxide units. The number of oxyalkylene units present in the polyoxyalkylenated chain can range, for example, from 3 to 100 units, further, for example, from 3 to 50 units, and even further, for example, from 7 to 25 units.

Among these copolymers, non-limiting mention may be made of:

crosslinked and noncrosslinked, neutralized and non-neutralized copolymers comprising from 15% to 60% by weight of AMPS units, relative to the total weight of the copolymer, and from 40% to 85% by weight of ($C_8$–$C_{16}$) alkyl(meth)acrylamide units, relative to the total weight of the copolymer, and from 40% to 85% by weight of ($C_8$–$C_{16}$)alkyl(meth)acrylate units, relative to the total weight of the copolymer, such as those described in Patent Application No. EP-A-750 899;

terpolymers comprising from 10 mol % to 90 mol % of acrylamide units, relative to the total weight of the copolymer, from 0.1 mol % to 10 mol % of AMPS units, relative to the total weight of the copolymer and from 5 mol % to 80 mol % of n-($C_6$–$C_{18}$)alkylacrylamide units, relative to the total weight of the copolymer, such as those described in U.S. Pat. No. 5,089,578;

crosslinked and noncrosslinked copolymers of partially and totally neutralized AMPS and of dodecyl methacrylate and of n-dodecylmethacrylamide, such as those described in the Morishima articles mentioned above.

Further examples include, copolymers comprising of 2-acrylamido-2-methylpropanesulphonic acid (AMPS) units of formula (II) below:

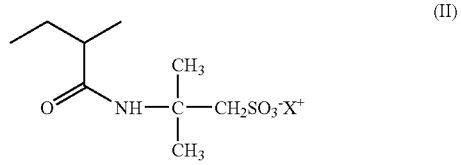

(II)

wherein X+ is a proton chosen from, alkali metal cations, alkaline-earth metal cations and ammonium ions, and of units of formula (III) below:

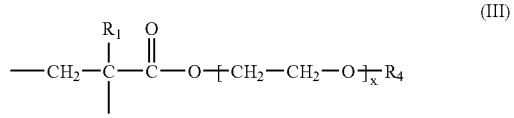

(III)

wherein x is an integer ranging from 3 to 100, for example, from 5 to 80, such as from 7 to 25; $R_1$ is chosen from hydrogen and linear and branched $C_1$–$C_6$ alkyl groups (such as methyl) and $R_4$ is chosen from linear and branched $C_6$–$C_{22}$ hydrocarbon-based chains, such as $C_{10}$–$C_{22}$ alkyls.

Even further examples include copolymers wherein x=25, $R_1$ is methyl and $R_4$ is n-dodecyl; which are described in the Morishima articles mentioned above.

In one embodiment, X+ is an ion chosen from sodium and ammonium.

The molar percentage concentration of the units of formula (II) and of the units of formula (III) in the copolymers may vary as a function of the desired cosmetic use and of the desired rheological properties of the formulation. For example, for the most hydrophobic copolymers, the molar proportion of units of formula (I) or (III) ranges from 50.1% to 99.9% by weight, relative to the total weight of the copolymer, for example, from 70% to 95% by weight, relative to the total weight of the copolymer, and further, for example, from 80% to 90% by weight, relative to the total weight of the copolymer.

For example, for the hydrophobic copolymers, the molar proportion of units of formula (I) or (III) ranges from 0.1% to 50% by weight, relative to the total weight of the copolymer, for example, from 5% to 25% by weight, relative to the total weight of the copolymer, and further, for example, from 10% to 20% by weight, relative to the total weight of the copolymer.

The monomer distribution in the copolymers of the invention may be chosen, for example, from alternating, block (including multiblock) and random monomer distributions.

In one embodiment the amphiphilic copolymers, as disclosed herein, may be obtained according to the standard free-radical polymerization processes in the presence of at least one initiator, such as azobisisobutyronitrile (AIBN), azobisdimethylvaleronitrile, ABAH (2,2-azobis[2-amidinopropane]hydrochloride), organic peroxides, such as dilauryl peroxide, benzoyl peroxide, and tert-butyl hydroperoxide, mineral peroxide compounds, such as potassium persulphate and ammonium persulphate, and $H_2O_2$ optionally in the presence of reducing agents.

For example, the copolymers can be obtained by free-radical polymerization in tert-butanol medium in which they precipitate.

In one embodiment, the reaction may be performed at a temperature ranging from 0 to 150° C., for example, from 10 to 100° C., either at atmospheric pressure or under reduced pressure. It may also be performed under inert atmosphere, such as under nitrogen.

According to the above process, 2-acrylamido-2-methylpropanesulphonic acid and sodium and ammonium salts thereof can, for example, be polymerized with at least one (meth)acrylic acid ester and $C_{10}$–$C_{18}$ alcohol oxyethylenated with 8 mol of ethylene oxide (8 EO) (Genapol® C-080 from the company Hoechst/Clariant), $C_{11}$ oxo alcohol oxyethylenated with 8 mol of ethylene oxide (Genapole® UD-080 from the company Hoechst/Clariant), $C_{11}$ oxo alcohol oxyethylenated with 7 mol of ethylene oxide (Genapole® UD-070 from the company Hoechst/Clariant), $C_{12}$–$C_{14}$ alcohol oxyethylenated with 7 mol of ethylene oxide (Genapole® LA-070 from the company Hoechst/Clariant), $C_{12}$–$C_{14}$ alcohol oxyethylenated with 9 mol of ethylene oxide (Genapol® LA-090 from the company Hoechst/Clariant), $C_{12}$–$C_{14}$ alcohol oxyethylenated with 11 mol of ethylene oxide (Genapol® LA-110 from the company Hoechst/Clariant), $C_{16}$–$C_{18}$ alcohol oxyethylenated with 8 mol of ethylene oxide (Genapol® T-080 from the company Hoechst/Clariant), $C_{16}$–$C_{18}$ alcohol oxyethylenated with 15 mol of ethylene oxide (Genapol® T-150 from the company Hoechst/Clariant), $C_{16}$–$C_{18}$ alcohol oxyethylenated with 11 mol of ethylene oxide (Genapole® T-110 from the company Hoechst/Clariant), $C_{16}$–$C_{18}$ alcohol oxyethylenated with 20 mol of ethylene oxide (Genapol® T-200 from the company Hoechst/Clariant), $C_{16}$–$C_{18}$ alcohol oxyethylenated with 25 mol of ethylene oxide (Genapol® T-250 from the company Hoechst/Clariant), $C_{18}$–$C_{22}$ alcohol oxyethylenated with 25 mol of ethylene oxide and $C_{16}$–$C_{18}$ iso alcohol oxyethylenated with 25 mol of ethylene oxide.

The viscosities (measured at 25° C. using a Brookfield viscometer, needle No. 7) of the aqueous 1% solutions range, for example, from 20 000 mPa·s to 100 000 mPa·s and further, for example, from 60 000 mPa·s to 70 000 mPa·s.

In one embodiment, the copolymer is present in an amount ranging from 0.005% to 15% by weight, relative to the total weight of the composition, for example, from 0.05% to 7.5% by weight, relative to the total weight of the composition, and further, for example, from 0.1% to 5% by weight, relative to the total weight of the composition.

Oil Phase of the Emulsion

The oil phase of the emulsion may, for example, comprise at least one fatty alcohol.

As used herein, the term "fatty alcohol" means any saturated or unsaturated, linear or branched fatty alcohol. Among these fatty alcohols, $C_{12}$–$C_{22}$ alcohols may, for example, be used.

For example, the at least one fatty alcohol may be chosen from lauryl alcohol, cetyl alcohol, stearyl alcohol, oleyl alcohol, behenyl alcohol, linoleyl alcohol, undecylenyl alcohol, palmitoleyl alcohol, linolenyl alcohol, arachidonyl alcohol and erucyl alcohol. Cetyl alcohol may, for example, be used.

In one embodiment, the at least one hydrogen peroxide oil-in-water emulsion, disclosed herein, the at least one fatty alcohol may be present in an amount ranging from about 0.1% to 30% by weight, relative to the total weight of the at least one hydrogen peroxide oil-in-water emulsion, and, further, for example, from about 0.5% to 15% by weight, relative to the total weight of the at least one hydrogen peroxide oil-in-water emulsion.

Additives

The at least one hydrogen peroxide oil-in-water emulsion may also comprise at least one additive that is common in the field, for example, at least one additive chosen from sequestering agents, such as ethylenediaminetetraacetic acid, pentasodium pentetate (CTFA name) and etidronic acid; hydrogen peroxide stabilizers, such as alkali metal (for instance, sodium and potassium) stannate and pyrophosphate salts, and sodium salicylate; colorants, fragrances; antifoams; and cationic and amphoteric substantive polymers, such as those described above.

In one embodiment, the hydrogen peroxide in the at least one hydrogen peroxide oil-in-water emulsion is present in an amount ranging from 1% to 12% by weight as hydrogen peroxide titre, for example, from 2% to 12% by weight as hydrogen peroxide titre, and, further, for example, from 2.7% to 12% by weight as hydrogen peroxide titre.

The hydrogen peroxide in the at least one ready-to-use bleaching composition may be present, for example, in an amount ranging from 1% to 12% by weight as hydrogen peroxide titre, further, for example, from 2% to 9% by weight as hydrogen peroxide titre, and even further, for example, from 2% to 6% by weight as hydrogen peroxide titre.

For example, the pH of the at least one hydrogen peroxide oil-in-water emulsion may range from 1 to 6 and, further, for example, from 2 to 4.

In one embodiment, the acidic pH ensures the stability of the hydrogen peroxide in the at least one hydrogen peroxide oil-in-water emulsion. The acidic pH may be obtained by using at least one acidifying agent, for example, chosen from hydrochloric acid, acetic acid, phosphoric acid, lactic acid, citric acid, salicylic acid and boric acid.

In addition, the pH may be conventionally adjusted, if necessary, by adding at least one basifying agent, for example, chosen from aqueous ammonia, monoethanolamine, diethanolamine, triethanolamine, isopropanolamine, 1,3-diaminopropane, alkaline and ammonium (bi)carbonate, organic carbonate, such as guanidine carbonate, andalkaline hydroxide, it being possible, obviously, for all these compounds to be taken alone or as a mixture.

In one embodiment, the at least one hydrogen peroxide oil-in-water emulsion is prepared by mixing at room temperature the hydrogen peroxide and the other ingredients of the aqueous phase of the oil-in-water emulsion and then preparing the emulsion by adding the oil phase of the emulsion, at a temperature above room temperature.

One example of a process for preparing the ready-to-use bleaching composition, as disclosed herein, comprises mixing the at least one anhydrous bleaching composition and the at least one hydrogen peroxide oil-in-water emulsion. This mixing may be performed immediately before applying the product to the fibers to be bleached.

In one embodiment, the at least one anhydrous bleaching composition is mixed with about 0.5 to about 10 equivalents by weight, of the at least one hydrogen peroxide oil-in-water emulsion.

The pH of the ready-to-use composition disclosed herein may range, for example, from 4 to 12, further, for example, from 7 to 11.5 and even further, for example, from 8 to 11.

Further disclosed herein, is a process for bleaching human keratin fibers, such as hair, comprising applying the ready-to-use bleaching composition to the area of the wet or dry human keratin fibers to be bleached; leaving the composition to act for a leave-in time that is sufficient to obtain the desired bleaching result; removing the composition, from the human keratin fibers, by rinsing with water, washing the human keratin fibers with shampoo and then optionally drying the human keratin fibers.

The leave-in time may range, for example, from 1 to 60 minutes and, further, for example, from 10 to 50 minutes.

Further disclosed herein, is a multi-compartment device or "kit" for performing the process for bleaching human keratin fibers.

This device comprises at least two compartments, wherein at least one compartment comprises:
i) at least one anhydrous bleaching composition comprising
   at least one peroxygenated salt,
   at least one alkaline agent, and
   from 15% to 35% by weight of at least one inert organic liquid, and
ii) at least one oxidizing composition in the form of a hydrogen peroxide oil-in-water emulsion comprising
   at least one surfactant chosen from nonionic and anionic surfactants and
   at least one copolymer comprising at least one hydrophobic unit and at least one unit derived from at least one ethylenically unsaturated monomer comprising at least one sulphonic group, in free or partially or totally neutralized form.

In one embodiment, the at least one anhydrous bleaching composition is in paste form.

In one embodiment, the at least one oxidizing composition is in the form of a hydrogen peroxide oil-in-water emulsion.

Non-limiting examples of the present invention will now be given.

EXAMPLES

Bleaching Composition A in Anhydrous Paste Form
Composition A below was prepared by mixing together the following compounds:

| | Amount (g %) |
|---|---|
| Potassium persulphate | 41.3 |
| Sodium disilicate | 18 |
| Ammonium chloride | 2.2 |
| Ammonium sulphate | 2 |
| EDTA | 0.2 |
| Hexamethyl diisocyanate/polyethylene glycol copolymer comprising α and ω stearyl polyoxyethylene end groups sold under the name Nuvis FX 1100 by the company Servo Delden | 0.5 |
| Weakly crosslinked carboxymethyl potato starch/sodium salt | 1 |
| Guar gum | 0.5 |
| Xanthan gum | 2 |
| Titanium oxide | 1 |
| Sodium cetostearyl sulphate | 2 |
| Sodium lauryl sulphate | 2 |
| Magnesium stearate | 2 |
| Ultramarine | 0.5 |
| Isopropyl myristate, sold under the name Isopropyl Myristate by the company Cognis | 24.2 |
| Fumed silica of hydrophilic nature, sold under the name Aerosil 300 by the company Degussa Huls | 0.6 |

Oxidizing Compositions (O/W Emulsions)
The emulsions below were prepared by mixing the following compounds:

| | B (g %) | C (g %) | D (g %) | E (g %) |
|---|---|---|---|---|
| Cetyl alcohol | 6 | 6 | 6.4 | 6 |
| Sodium lauryl sulphate | 1.2 | 1.2 | 1.2 | 1.6 |
| Polyglycerolated oleyl alcohol (2 mol) | 0.5 | 0.5 | 0.5 | 0.5 |
| Polyglycerolated oleyl alcohol (4 mol) | 0.5 | 0.5 | 0.5 | 0.5 |

-continued

| | B (g %) | C (g %) | D (g %) | E (g %) |
|---|---|---|---|---|
| Glycerol | 2 | 2 | 2 | 2 |
| AMPS polymer (*) | 0.4 | / | / | / |
| Tetrasodium pyrophosphate | 0.04 | 0.04 | 0.04 | 0.04 |
| Sodium etidronate | 0.2 | 0.2 | 0.2 | 0.2 |
| Aqueous 50% hydrogen peroxide solution | 18 | 18 | 18 | 18 |
| 85% phosphoric acid | qs pH3 | qs pH3 | qs pH3 | qs pH3 |
| Water | qs 100 g | qs 100 g | qs 100 g | qs 100 g |

(*) ** AMPS (80)/methacrylic ester of $C_{16}$–$C_{18}$ alcohol oxyethylenated with 25 mol of ethylene oxide (20), crosslinked with trimethylolpropane triacrylate, as prepared and described in Patent Application No. FR 2 818 543.

Ready-to-use aqueous bleaching compositions
Comp. A/B: 20 g of bleaching composition A+30 g of oxidizing composition B
Comp. A/C: 20 g of bleaching composition A+30 g of oxidizing composition C
Comp. A/D: 20 g of bleaching composition A+30 g of oxidizing composition D
Comp. A/E: 20 g of bleaching composition A+30 g of oxidizing composition E
The compositions were obtained by mixing.

Evaluation of the speed of mixing of the ready-to-use aqueous bleaching compositions
Evaluation of the mixing time in seconds (cf. via a chronometer)
Starting the chronometer when the spatula enters the mixture
Stopping the chronometer when the mixtures are smooth and uniform
Evaluation by a panel of 5 individuals

| | Comp. A/B | Comp. A/C | Comp. A/D | Comp. A/E |
|---|---|---|---|---|
| Evaluation of the mixing time/mean (seconds) | 73 | 90 | 87 | 92 |
| Standard deviation (seconds) | 5 | 5 | 6 | 4 |

The mixture of compositions A and B (Comp. A/B), as disclosed herein, was significantly faster to prepare.

Furthermore, the ready-to-use bleaching composition Comp. A/B applied easily and quickly. It showed very good adhesion. It did not run outside the areas of hair that it was desired to bleach. Finally, it gave strong and uniform bleaching, while at the same time afforded very good cosmetic properties.

What is claimed is:
1. A composition comprising:
i) at least one anhydrous bleaching composition comprising
   at least one peroxygenated salt,
   at least one alkaline agent, and
   from 15% to 35% by weight of at least one inert organic liquid, and
ii) at least one oxidizing composition comprising
   at least one surfactant chosen from nonionic and anionic surfactants and at least one copolymer comprising at least one hydrophobic unit and at least one unit derived from at least one ethylenically unsaturated monomer comprising at least one sulphonic group, in free or partially or totally neutralized form.

2. The composition according to claim 1, wherein the composition is for bleaching human keratin fibers.

3. The composition according to claim 2, wherein the human keratin fibers are hair.

4. The composition, according to claim 2, wherein the composition is obtained by mixing before using it.

5. The composition according to claim 1, wherein the at least one anhydrous bleaching composition is in paste form.

6. The composition according to claim 1, wherein the at least one oxidizing composition is in the form of a hydrogen peroxide oil-in-water emulsion.

7. The composition according to claim 1, wherein the at least one inert organic liquid is chosen from polydecenes, carboxylic acid monoesters, carboxylic acid polyesters, sugar monoesters of $C_8$–$C_{30}$ acids, polyesters of $C_8$–$C_{30}$ acids, cyclic ethers, cyclic esters, silicone oils, mineral oils and plant oils.

8. The composition according to claim 1, wherein the at least one inert organic liquid is chosen from esters of $C_8$–$C_{30}$ acids and of saturated, linear and branched $C_3$–$C_6$ monoalcohols.

9. The composition according to claim 1, wherein the at least one peroxygenated salt is chosen from alkali metal persulphates, alkaline-earth metals persulphates, perborates, percarbonates and peroxides.

10. The composition according to claim 9, wherein the at least one peroxygenated salt is chosen from sodium persulphates and potassium persulphates.

11. The composition according to claim 1, wherein the at least one peroxygenated salt is present in the at least one anhydrous bleaching composition in an amount ranging from 10% to 70% by weight, relative to the total weight of the at least anhydrous bleaching composition.

12. The composition according to claim 11, wherein the at least one peroxygenated salt is present in the at least one anhydrous bleaching composition in an amount ranging from 20% to 60% by weight, relative to the total weight of the at least one anhydrous bleaching composition.

13. The composition according to claim 1, wherein the at least one peroxygenated salt is present in an amount ranging from 5% to 35% by weight, relative to the total weight of the composition.

14. The composition according to claim 13, wherein the at least one peroxygenated salt is present in an amount ranging from 10% to 30% by weight, relative to the total weight of the composition.

15. The composition according to claim 1, wherein the at least one alkaline agent is chosen from urea; ammonium salts; alkali metal silicates, alkaline-earth metal silicates, phosphates and carbonates.

16. The composition according to claim 1, wherein the at least one alkaline agent is present in the at least one anhydrous bleaching composition in an amount ranging from 0.01% to 40% by weight, relative to the total weight of the at least one anhydrous bleaching composition.

17. The composition according to claim 16, wherein the at least one alkaline agent is present in the at least one anhydrous bleaching composition in an amount ranging from 0.1% to 30% by weight, relative to the total weight of the at least one anhydrous bleaching composition.

18. The composition according to claim 1, wherein the at least one alkaline agent is present in an amount ranging from 0.005% to 20% by weight, relative to the total weight of the composition.

19. The composition according to claim 18, wherein the at least one alkaline agent is present in an amount ranging from 0.05% to 15% by weight, relative to the total weight of the composition.

20. The composition according to claim 1, wherein the at least one anhydrous bleaching composition further comprises at least one surfactant chosen from nonionic, anionic, amphoteric, zwitterionic and cationic surfactants.

21. The composition according to claim 1, wherein the at least one anhydrous bleaching composition further comprises at least one water-soluble thickener not comprising a hydrophobic chain.

22. The composition according to claim 21, wherein the at least one water-soluble thickener in the at least one anhydrous bleaching composition is present in an amount ranging from 0.01% to 30% by weight, relative to the total weight of the at least one anhydrous bleaching composition.

23. The composition according to claim 1, wherein the at least one anhydrous bleaching composition further comprises at least one amphiphilic polymer comprising at least one hydrophobic chain.

24. The composition according to claim 23, wherein the at least one amphiphilic polymer is different from the at least one copolymer present in the at least one oxidizing composition.

25. The composition according to claim 23, wherein the at least one amphiphilic polymer comprising at least one hydrophobic chain is present in an amount ranging from 0.01% to 30% by weight, relative to the total weight of the composition.

26. The composition according to claim 1, wherein the at least one anhydrous bleaching composition comprises less than 1% by weight of water, relative to the total weight of the at least one anhydrous bleaching composition.

27. The composition according to claim 26, wherein the at least one anhydrous bleaching composition comprises less than 0.5% by weight of water, relative to the total weight of the at least one anhydrous bleaching composition.

28. The composition according to claim 1, wherein the at least one copolymer of the oxidizing composition comprises at least one unit derived from at least one ethylenically unsaturated monomer comprising at least one sulphonic group chosen from vinylsulphonic, styrenesulphonic, (meth) acrylamido(C1–C22)alkylsulphonic, and N-(C1–C22)alkyl (meth)acrylamido(C1–C22)alkylsulphonic acids.

29. The composition according to claim 28, wherein the N-(C1–C22)alkyl(meth)acrylamido(C1–C22)alkylsulphonic acid is chosen from undecylacrylamidomethanesulphonic acid.

30. The composition according to claim 1, wherein the at least one hydrophobic unit, of the at least one copolymer, comprises from 6 to 50 carbon atoms.

31. The composition according to claim 30, wherein the at least one hydrophobic unit, of the at least one copolymer, comprises from 6 to 22 carbon atoms.

32. The composition according to claim 31, wherein the at least one hydrophobic unit, of the at least one copolymer, comprises from 6 to 18 carbon atoms.

33. The composition according to claim 32, wherein the at least one hydrophobic unit, of the at least one copolymer, comprises from 12 to 18 carbon atoms.

34. The composition according to claim 1, wherein the at least one copolymer is present in an amount ranging from 0.005% to 15% by weight, relative to the total weight of the composition.

35. The composition according to claim 34, wherein the at least one copolymer is present in an amount ranging from 0.05% to 7.5% by weight, relative to the total weight of the composition.

36. The composition according to claim 35, wherein the at least one copolymer is present in an amount ranging from 0.1% to 5% by weight, relative to the total weight of the composition.

37. The composition according to claim 1, wherein the at least one oxidizing composition comprises
at least one anionic surfactant chosen from alkyl sulphates, alkyl ether sulphates, alkylamido ether sulphates, alkylarylpolyether sulphates, monoglyceride sulphates, alkyl sulphonates, alkyl phosphates, alkylamide sulphonates, alkylaryl sulphonates, α-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates, ($C_6$–$C_{24}$)alkyl sulphoacetates, ($C_6$–$C_{24}$)acyl sarcosinates, and ($C_6$–$C_{24}$acyl glutamates, ($C_6$–$C_{24}$)alkylpolyglycoside carboxylic esters, acyl isethionates and N-acyl taurates, fatty acid salts, alkyl D-galactoside uronic acids and their salts, polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$) alkylamido ether carboxylic acids and their salts, and
at least one nonionic surfactant chosen from polyethoxylated and polypropoxylated, alkylphenols, alpha-diols and alcohols comprising at least one fatty chain, copolymers of ethylene oxide and of propylene oxide, condensates of ethylene oxide and of propylene oxide with fatty alcohols, polyethoxylated fatty amides, mono- and polyglycerolated fatty alcohols, polyglycerolated fatty amides, oxyethylenated fatty acid esters of sorbitan, fatty acid esters of sucrose, fatty acid esters of polyethylene glycol, alkylpolyglycosides, N-alkylglucamine derivatives, and amine oxides.

38. The composition according to claim 37, wherein the at least one fatty chain of the alcohol comprising at least one fatty chain, comprises from 6 to 24 carbon atoms.

39. The composition according to claim 37, wherein the amine oxides are chosen from ($C_{10}$–$C_{14}$)alkylamine oxides and N-acylaminopropylmorpholine oxides.

40. The composition according to claim 20, wherein the at least one surfactant is present in an amount ranging from 0.05% to 30% by weight, relative to the total weight of the composition.

41. The composition according to claim 40, wherein the at least one surfactant is present in an amount ranging from 0.1% to 20% by weight, relative to the total weight of the composition.

42. The composition according to claim 6, wherein the oil phase of the oil-in-water emulsion comprises at least one fatty alcohol.

43. The composition according to claim 6, wherein the hydrogen peroxide in the composition is present in an amount ranging from 1% to 12% as hydrogen peroxide titre.

44. The composition according to claim 43, wherein the hydrogen peroxide in the composition is present in an amount ranging from 2% to 9% as hydrogen peroxide titre.

45. The composition according to claim 44, wherein the hydrogen peroxide in the composition is present in an amount ranging from 2% to 6% as hydrogen peroxide titre.

46. The composition according to claim 1, wherein the pH of the oil-in-water emulsion ranges from 1 to 6.

47. The composition according to claim 46, wherein the pH of the oil-in-water emulsion ranges from 2 to 4.

48. The composition according to claim 1, wherein the pH of the composition ranges from 4 to 12.

49. The composition according to claim 48, wherein the pH of the composition ranges from 7 to 11.5.

50. The composition according to claim 49, wherein the pH of the composition ranges from 8 to 11.

51. A process for preparing a ready-to-use composition for bleaching human keratin fibers comprising:
i) at least one anhydrous bleaching composition comprising
at least one peroxygenated salt,
at least one alkaline agent, and
from 15% to 35% by weight of at least one inert organic liquid, and
ii) at least one oxidizing composition comprising
at least one surfactant chosen from nonionic and anionic surfactants and
at least one copolymer comprising at least one hydrophobic unit and at least one unit derived from at least one ethylenically unsaturated monomer comprising at least one sulphonic group, in free or partially or totally neutralized form.

52. The process according to claim 51, wherein the human keratin fibers are hair.

53. The process, according to claim 51, wherein the process is obtained by mixing before using it.

54. The process according to claim 51, wherein the at least one anhydrous bleaching composition is in paste form.

55. The process according to claim 51, wherein the at least one oxidizing composition is in the form of a hydrogen peroxide oil-in-water emulsion.

56. A process for bleaching human keratin fibers, comprising
(1) applying, to the area of wet or dry human keratin fibers to be bleached, at least one ready-to-use bleaching composition comprising
i) at least one anhydrous bleaching composition comprising
at least one peroxygenated salt,
at least one alkaline agent, and
from 15% to 35% by weight of at least one inert organic liquid, and
ii) at least one oxidizing composition comprising
at least one surfactant chosen from nonionic and anionic surfactants and
at least one copolymer comprising at least one hydrophobic unit and at least one unit derived from at least one ethylenically unsaturated monomer comprising at least one sulphonic group, in free or partially or totally neutralized form,
(2) leaving the composition to act for a leave-in time that is sufficient to obtain the desired bleaching result;
(3) removing the composition from the human keratin fibers by rinsing with water,
(4) washing the human keratin fibers with shampoo and optionally drying the human keratin fibers.

57. The process according to claim 56, wherein the human keratin fibers are hair.

58. The process according to claim 56, wherein the at least one anhydrous bleaching composition is in paste form.

59. The process according to claim 56, wherein the at least one oxidizing composition is in the form of a hydrogen peroxide oil-in-water emulsion.

60. The process according to claim 56, wherein the leave-in time ranges from 1 to 60 minutes.

61. The process according to claim 60, wherein the leave-in time ranges from 10 to 50 minutes.

62. A multi-compartment device or "kit" comprising at least two compartments, wherein, at least one compartment comprises:

i) at least one anhydrous bleaching composition comprising at least one peroxygenated salt, at least one alkaline agent, and from 15% to 35% by weight of at least one inert organic liquid, and ii) at least one oxidizing composition comprising at least one sulfactant chosen from nonionic and anionic surfactants and at least one copolymer comprising at least one hydrophobic unit and at least one unit derived from at least one ethylenically unsaturated monomer comprising at least one sulphonic group, in free or partially or totally neutralized form.

63. The kit according to claim 62, wherein the at least one anhydrous bleaching composition is in paste form.

64. The kit according to claim 62, wherein the at least one oxidizing composition is in the form of a hydrogen peroxide oil-in-water emulsion.

* * * * *